United States Patent [19]
Taylor et al.

[11] Patent Number: 5,733,759
[45] Date of Patent: Mar. 31, 1998

[54] METHODS FOR THE REGULATION OF PLANT FERTILITY

[75] Inventors: Loverine P. Taylor; Yinyuan Mo, both of Pullman, Wash.

[73] Assignee: Washington State University Research Foundation, Pullman, Wash.

[21] Appl. No.: 179,883

[22] Filed: Jan. 11, 1994

Related U.S. Application Data

[63] Continuation of Ser. No. 847,908, Mar. 9, 1992, abandoned.

[51] Int. Cl.$^6$ .............. C12N 15/82; C12N 5/10; C12N 9/00; A01H 1/00
[52] U.S. Cl. .......... 435/172.3; 435/91.1; 435/172.1; 435/183; 435/320.1; 435/375; 435/377; 800/200; 800/205; 800/230; 800/235; 800/250; 47/58; 47/DIG. 1
[58] Field of Search ............ 800/230, 205, 800/200, 235, 250; 435/172.3, 172.1, 91.1, 183, 320.1, 375, 377; 47/58.03, DIG. 1, 58

[56] References Cited

U.S. PATENT DOCUMENTS 5,432,068  7/1995  Albertsen et al. ............... 435/172.3

FOREIGN PATENT DOCUMENTS

| | | | |
|---|---|---|---|
| 0465024 | 1/1992 | European Pat. Off. | ........ C12N 15/82 |
| 9012107 | 10/1990 | WIPO . | |
| WO 90/12084 | 10/1990 | WIPO | ............... C12N 5/00 |
| WO 92/18625 | 10/1992 | WIPO . | |

OTHER PUBLICATIONS

E. Szember et al. (Abstract) Fruit Science Reports, vol. 18 (2) 91, pp. 85–90.
H. Riele et al PNAS, vol. 89, (Jun. 1992) pp. 5128–5132.
D. Grierson et al., in Genetic Engineering of Crop Plants, ed by G. Lycett & D. Grierson, London, Butterworths, 1990, pp. 115–125.
T. McGarry et al, PNAS, vol. 83, (Jan. 1986) pp. 399–403.
J. Eckel et al. PNAS, vol. 83 (Aug. 1986) pp. 5372–5376.
van der Krol, A., et al. Nature, vol. 333 (Jun. 30, 1988) pp. 866–869.
Harborne, J. B., in Encyclopedia of Plant Physiology, New Series, vol. 8, Ed. by E. A. Bell et al., Springer Verlag, Berlin, 1980, pp. 340–350.
Sedgley, M. (Abstract) Annals of Botany (London), vol. 39 (164) (1975), pp. 1091–1095.
Mariani, C., et al. Nature, vol. 347 (Oct. 25, 1990) pp. 737–741.
Forkmann, G., et al Planta, vol. 161 (1984) pp. 261–265.
Franken, P., et al. Maize Gen. Coop. Newsletter, vol. 65 (Mar. 1, 1991) p. 51.
Bell, E.A. et al. (eds.), "Secondary Plant Products," published 1980 by Springer–Verlag (Berlin), pp. 340–350.
Benfey, P.N. et al., "Regulated Genes in Transgenic Plants," Science 244:174–181, 1989.

Coe, E., et al. J. Hevedity, vol. 72 (1981) pp. 318–320 (abstract).
van der Krol, A., et al. Nature, vol. 333 (1988) pp. 866–869.
Franken, P., et al. Maize Genetics Cooperation Newsletter, vol. 65 (Mar. 1, 1991) p. 51.
Harborne, J.B., "Plant Phenolics", in Secondary Plant Products, ed. by E. Bell & B. Charlwood, Berlin, Springer–Verlag, 1980, pp. 340–350.
Forkmann, G., et al. Planta, vol. 161 (1984) pp. 261–265.
Dooner, H.K. et al., "Genetic and Developmental Control of Anthrocyanin Biosynthesis," *Annual Rev. Genet.*, 25:173–179 (partial article), 1991.
Mariani, C. et al., "Induction of male sterility in plants by a chimaeric ribonuclease gene," *Nature* 347:737–741, 1990.
Oeller, P.W. et al., "Reversible Inhibition of Tomato Fruit Senescence by Antisense RNA," *Science* 254:437–439, 1991.
Peacock, J., "Ways to pollen sterility," *Nature* 347:714–715, 1990.
Stam, M.E. et al., "Inhibition of flavonoid biosynthesis in petunia anthers by an antisense approach results in male sterility," in *Regulation of Flavonoid Gene Expression in Petunia Hybrida: cis–acting elements and trans–acting factors*, Chapter IV, Ingrid Maria van der Meer, ed., pp. 82–98, Drukkeriji FEBO, Enschede, 1991.
Ylstra, B. and A.J. van Tunen, "F1 hybrid seed production and flavonoids," *Prophyta*, Jun. 1992, pp. 56–58.

*Primary Examiner*—Charles C. P. Rories
*Attorney, Agent, or Firm*—Christensen O'Connor Johnson & Kindness PLLC

[57] ABSTRACT

Plants in which flavonol activity has been impaired are conditionally male fertile (CMF), and male fertility can be rescued or restored by providing fertility restoring flavonols at pollen sites in the plant. Although viable pollen is produced by flavonol deficient plants, pollen germination and tube growth are severely reduced both in vivo and in vitro, resulting in plants which are self sterile. However, by contacting pollen of the plant with an amount of a fertility restoring flavonol effective to enhance germination of the pollen, full pollen germination and tube growth may be restored. Useful fertility restoring flavonols include compounds of the formula:

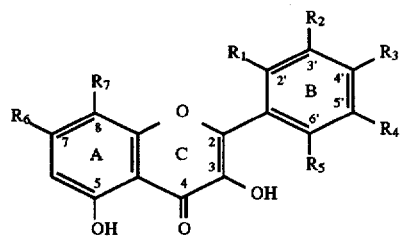

wherein $R_1$, $R_2$, $R_3$, $R_4$, $R_5$, $R_7$, and $R_8$, are hydrogen, hydroxyl or alkoxy having from 1 to 3 carbon atoms. Particularly preferred flavonols include galangin, kaempferol, iso-rhamnetin, quercetin and morin.

5 Claims, 6 Drawing Sheets

PETUNIA
DOMINANT STERILITY
MAIZE
RECESSIVE STERILITY
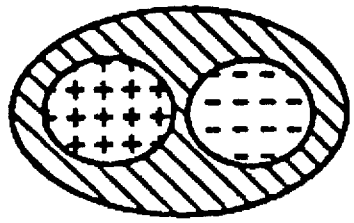 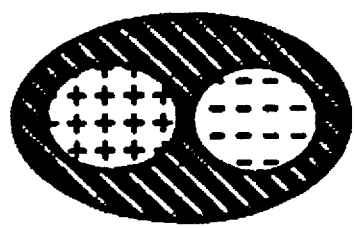
100 % STERILE POLLEN   100% FERTILE POLLEN
*Fig. 1A.*  *Fig. 1B.*

V26　　　　　O2425.1
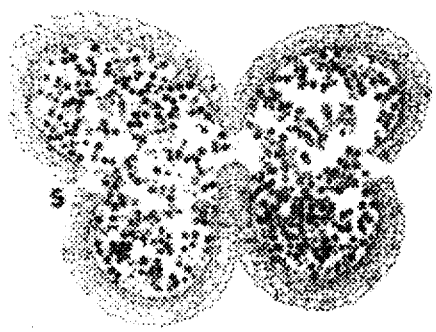
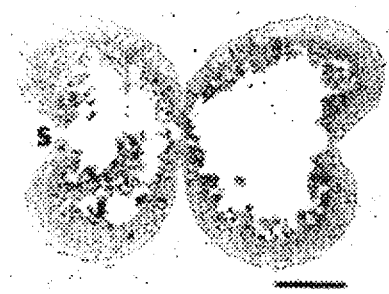
fig.3A.1
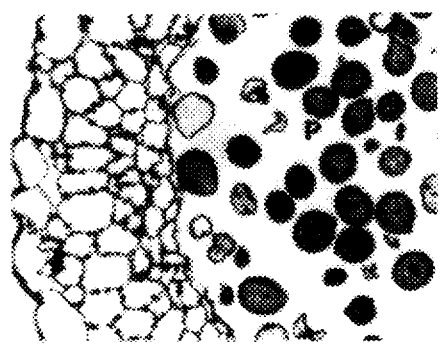
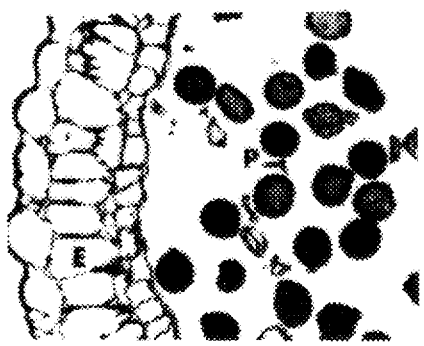
fig.3B.2
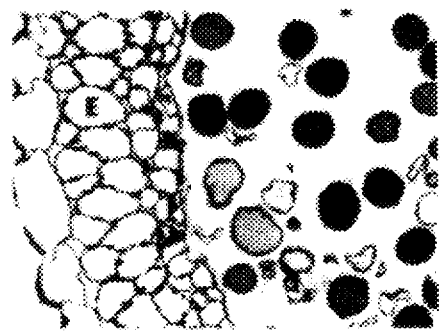
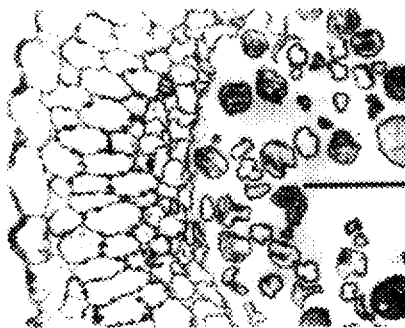
fig.3C.3
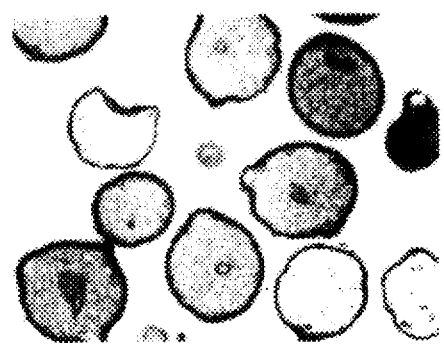
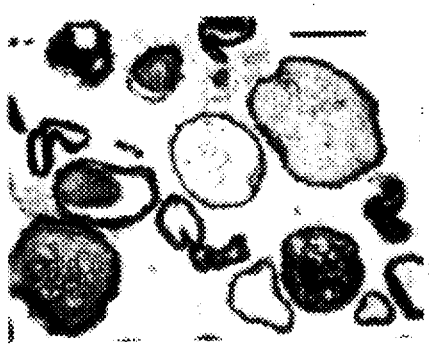
fig.3D.4

METHODS FOR THE REGULATION OF PLANT FERTILITY

This application is a continuation application based on prior application Ser. No. 07/847,908, filed on Mar. 9, 1992, now abandoned.

CROSS REFERENCES TO RELATED APPLICATIONS

1. Field of the Invention

This invention relates to methods for the regulation of fertility in plants, and more particularly to the creation of flavonoid-deficient, conditionally male fertile plants by blocking the activity of flavanone-3-hydroxylase in the plants, and to the restoration of fertility in flavonoid-deficient, conditionally male fertile plants by providing fertility restoring flavonols at the plant pollen sites.

2. Background of the Invention

Successful fertilization in higher plants is central not only to the perpetuation of a species but also provides the large populations that are the source of variation and competition that drive natural selection. In the post-dispersal phase of male gametophyte development, pollen germinates on the stigma and extrudes a tube through a germination pore in the pollen wall. In angiosperms, the growing pollen tube is a conduit for the migration of the two sperm cells through the stylar tissue to the embryo sac where they fuse with the egg and central cells to form the zygote and endosperm, respectively (E. G. Cutter, 1978, *Plant Anatomy, Part 1, Experimentation and Interpretation*. E. Arnold, Eds., Addison Wesley, London, chap. 6.). Pollen development takes place within the anther and at maturity each grain is a multi-celled spore containing products of both sporophytic gene expression, arising from the inner layer of the anther wall (tapetum), and haploid gene expression from the vegetative cell within each grain (J. P. Mascarenhas, 1990, *Annu. Rev. Plant Physiol. Plant Mol Biol.* 41:317; J. P. Mascarenhas, 1989, *Plant Cell* 1:657). Although the process of microsporogenesis is well documented histologically, little is known of the molecular and biochemical factors that are involved in post-dispersal pollen function.

Flavonoids are an abundant class of small molecular weight (~300) plant-specific metabolites which share a common 15 carbon skeletal structure. Modification of the basic structure yields an extensive array of compounds that are classified by the oxidation state and substitution pattern of the various rings. Some classes are pigments (e.g., anthocyanins, chalcones, and particular flavonols and flavones) while other classes are colorless ultraviolet-absorbing compounds. The anthocyanins, particularly pelargonin, cyanidin, and delphinidin, are responsible for the red, blue and violet plant colors. Other pigmented flavonoids, the chalcones, and some flavonols and flavones, contribute significantly to the yellow, ivory and cream colored flowers. Pollen flavonoids have been identified in several species where they impart a distinctive yellow color to pollen and can account for a large percentage (2–5%) of the dry weight (R. Zerback, M. Bokel, H. Geiger, D. Hess, 1989, *Phytochemistry* 28:897; R. Wierinann and K. Vieth, 1983 *Protoplasma* 118:230). There is evidence that the pollen grain is a special environment for flavonoid biosynthesis and/or accumulation as several plant species have unique types of flavonoids in their pollen (O. Ceska and E. D. Styles, 1984, *Phytochemistry* 23:1822).

Plants having modified flavonoid pigmentation have been previously reported in the literature. For example, a maize mutant producing non-functional white rather than yellow pollen has been previously isolated and characterized (Coe E. H., McCormick S. M. and Modena S. A., 1981, "White pollen in maize," *J Hered* 72:318–320). The white pollen mutant sheds normal amounts of non-pigmented pollen which germinates on the silk, but no seed is set after most pollinations. The condition is sporophytically determined by the expression of stable recessive mutations at the two chalcone synthase (CHS) genes in maize, C2 and Whp. Recently, Agrobacterium-mediated introduction of a CHS transgene into a pigmented inbred petunia stock was reported to suppress the expression of the endogenous CHS gene(s), resulting in flower corollas completely lacking flavonoid pigmentation (Napoli C, Lemieux C and Jorgensen R, 1990, "Introduction of a chimeric chalcone synthase gene into petunia results in reversible co-repression of homologous genes in trans," *Plant Cell* 2:279–289). Because the expression of the CHS transgene is also suppressed in these plants, the term co-suppression has been used to describe this phenomenon (Jorgensen R, 1990, "Altered gene expression in plants due to trans interactions between homologous genes," *Trends Biotech* 8:340–344). The integrated transgene acts like an unlinked dominant inhibitor of the endogenous CHS gene(s) and leads to a complete block in the production of visible flavonoid pigments not only in flower petals but also reproductive organs.

Blockage of CHS gene expression results not only in flavonoid pigmentation deficiencies, but also in plants which are not fertile (Coe et al., 1981; Taylor et al., 1992, "Conditional Male Fertility in Chalcone Synthase Deficient Petunia," *J. Hered.* 83:11–17). It would be highly desirable to rescue fertility in CHS deficient plants and further to enable to be able to regulate plant fertility through control of an enzyme more closely linked to pollen fertility than CHS.

SUMMARY OF THE INVENTION

It has now been discovered that plants in which flavanone-3-hydroxylase (F3H) activity has been impaired in a manner which produces a flavonol deficiency are conditionally male fertile (CMF), and that male fertility can be rescued or restored by providing conditions under which pollen of the plants may be contacted with fertility restoring flavonols. F3H activity may be impaired by blocking F3H production in the plants, directly or indirectly, for example, by inactivating F3H naturally produced by the plants or by impairing the activity of a precursor enzyme, such as chalcone synthase (CHS) in the flavonol biosynthetic pathway. Although viable pollen is produced by F3H deficient plants, pollen germination and tube growth are severely reduced both in vivo and in vitro, resulting in plants which are self sterile. However, by providing conditions under which pollen of the plants may be contacted with fertility restoring flavonols, full pollen germination and tube growth ability of the plants may be restored. Suitable fertility restoring conditions include any conditions where the required flavonols are made available to the pollen of the plants, including, for example, by removal of the F3H impairing condition, restoration of F3H production in the plants, and the like. Alternatively, fertility of the plants may be rescued or restored by contacting pollen of the plants with an amount of a fertility restoring flavonol effective to enhance germination and/or tube growth of the pollen. Useful fertility restoring flavonols include compounds of the formula:

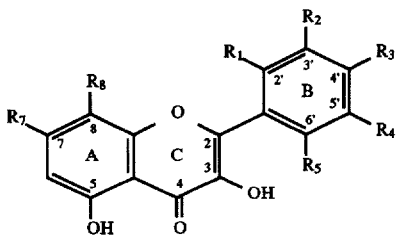

wherein $R_1$, $R_2$, $R_3$, $R_4$, $R_5$, $R_7$, and $R_8$, are hydrogen, hydroxyl or alkoxy having from 1 to 3 carbon atoms. Particularly preferred flavonols include galangin, kaempferol, iso-rhamnetin, quercetin and morin.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 is a schematic representation of sporophytic influence (diagonal lines) on the developing microspores in chalcone synthase (CHS) heterozygous plants. The lack of CHS function in the sporophyte is indicated by a white background (FIG. 1A) and the presence of CHS function is represented by a black background (FIG. 1B).

FIGS. 3A–3D are photographic representations of cross sections of developmentally identical anthers from inbred petunia line V26 (left column) and from CHS-deficient plant O2425.1 (right column), which had been harvested, fixed, embedded, transversely sectioned and stained with toluidine blue as described in Example 3. FIG. 3A shows whole anther sections immediately before dehiscence when CHS-deficient anthers are tan and shrunken. The bar in FIG. 3A represents 200 μm. FIG. 3B shows anther sections 48 hours before dehiscence when transgenic anthers are plump and white. FIG. 3C shows anther sections as FIG. 3A at the magnification of the representations of FIG. 3B. The bar in FIG. 3B represents 50 μm. FIG. 3D shows mature pollen at dehiscence. In FIG. 3, P represents pollen; E, endothecium; S, stomium; and C, cuticle.

DETAILED DESCRIPTION OF THE PREFERRED EMBODIMENT

Figures 2A, 2B:
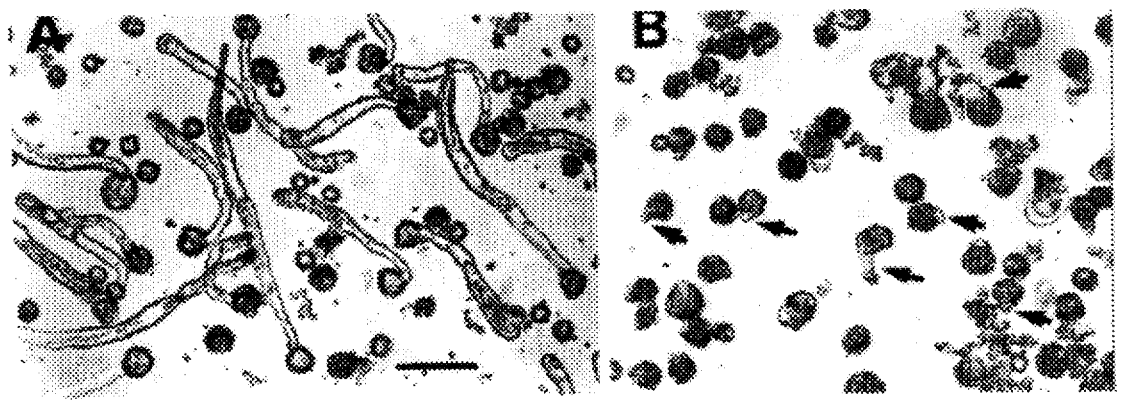
FIGS. 2A and 2B are photographic representations of in vitro germinating pollen from inbred petunia line V26 (FIG. 2A) and CHS-deficient plant O2425.1 (FIG. 2B), wherein the pollen from freshly dehiscent anthers was suspended in a liquid medium and photographed after growth at room temperature for 6 hours. The bar in FIG. 2A represents 25 μm. The arrows is FIG. 2B indicate pollen tubes attempting to germinate.

In accordance with one aspect of the present invention, plant fertility in a flavonoid-deficient, conditionally male fertile (CMF) plant is restored by providing conditions under which pollen of the plants may be contacted with fertility restoring flavonols. In an illustrative embodiment, suitable conditions may be obtained by contacting pollen of the plant with an amount of a fertility restoring flavonol effective to enhance germination and tube growth of the pollen of the plant. As used herein, the term flavonoid-deficient, conditionally male fertile or CMF plant is intended to include plants in which the chalcone synthase (CHS) or flavanone-3-hydroxylase (F3H) activity has been impaired, either naturally or transgenetically, to disrupt the natural production of flavonoids in the plant. Accordingly, flavonoid-deficient, conditionally male fertile plants will typically be pigment deficient, resulting in a white or pale coloration, and will typically be self sterile. Although the invention will be hereinafter described in detail in connection with CMF petunias and maize, other CMF plants may be similarly used in the practice of the invention.

In accordance with another aspect of the present invention, the fertility of plants may be regulated by blocking the activity of flavanone-3-hydroxylase (F3H) to produce a CMF plant that is normally self-sterile, but whose fertility may be rescued or restored by contacting pollen of the plant with a fertility restoring flavonol as described herein. In the natural flavonol biosynthetic pathway, chalcone synthase (CHS) condenses three molecules of malonyl-CoA and one molecule of p-coumaroyl to form chalcononaringenin, which is converted to naringenin spontaneously (at a low rate) and by the action of chalcone-flavanone isomerase (CHI). In the next step of the pathway, F3H catalyzes the addition of a hydroxyl group to the 3-position carbon of the C ring to produce a flavonol, which is required for fertility restoring activity in accordance with the present invention. The general pathway may be represented as follows:

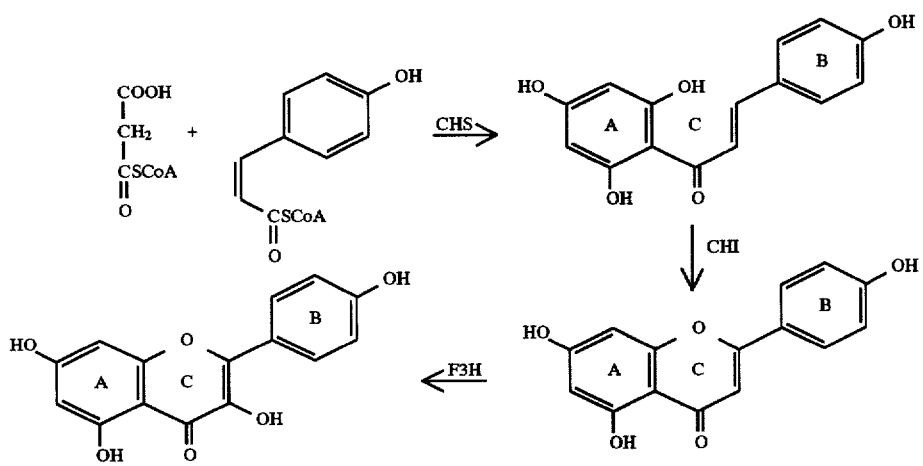

F3H is the rate limiting enzyme in the production of flavonols, and has been previously cloned from *Antirrhinum majus* (Martin, C., Prescott, A., Mackay, S., Bartlett, J. and Vrijlandt, E., 1991, "Control of biosynthesis in flowers of *Antirrhinum majus*," *The Plant J.* 1:37–39). Since flavonol aglycone compounds are required for male fertility, as described herein, any means which effectively blocks the F3H hydroxlation activity may be employed in the practice of the invention. Thus, for example, F3H substrates may be removed by blocking production of precursors in the biosynthetic pathway, or the expression of F3H, CHI or CHS may be blocked by interfering with gene expression. In another illustrative embodiment, plants having blocked flavonol production may be produced by expressing an antisense RNA in the plants which hybridizes to mRNA encoding or necessary for the expression of F3H or a precursor enzyme, such as CHI, in the plants. For example, a tapetal cell-specific promoter may be fused to the F3H gene in an antisense orientation, and the fusion construct may be introduced into plant cells, such as tobacco, petunia, tomato, or other plant cells, using known techniques, such as Agrobacterium-mediated transformation, particle gun bombardment, direct DNA introduction techniques and the like (see, for example, Napoli C, Lemieux C and Jorgensen R, 1990, "Introduction of a chimeric chalcone synthase gene into petunia results in reversible co-repression of homologous genes in trans," *Plant Cell* 2:279–289; Mariani, C., De Beuckleer, M., Truettner, J., Leemans, J. and Goldberg, R. B., 1990, "Induction of male sterility in plants by a chimeric ribonuclease gene," *Nature* 347:737–741; and Oeller, P. W., Min-Wong, L., Taylor, L. P., Pike, D. A., and Theologis, A., "Reversible inhibition of tomato fruit senescence by antisense RNA," *Science* 254:437–439). The tapetum promoter may be isolated by differential cDNA cloning (Goldberg, R. B., 1988, "Plants: novel developmental processes," *Science* 240:1460–1467) or by using a hybridization probe generated by polymerase chain reaction (PCR) amplification of genomic sequences (see Saiki, R. K., 1990, "Amplification of genomic DNA," in *PCR Protocols*, M. A. Innin, Felfand, D. H., Sninsky, J. J. and White, T. J., eds, Academic Press, San Diego, pp. 13–20) homologous to previously published tapetum-specific promoters. Alternatively, the F3H gene may be isolated by generating a hybridization probe using PCR oligonucleotide primers (see Saiki, R. K., 1990, supra) based on the published Antirrhinum F3H sequence. As a further alternative, the gene encoding F3H, CHI or CHS in a plant may be altered, mutated, removed, blocked or otherwise impaired to prevent expression of the F3H enzyme in the plant. For example, the gene encoding F3H in a plant may be deleted from the nuclear genome of the plant and replaced with the F3H gene operably linked to an inducible promoter as described in European patent application EP 0465024 published Jan. 8, 1992, to enable controlled unblocking of flavonol production and rescue of plant fertility by externally induced gene expression. In addition to blocking the synthesis of F3H in vivo, it will also be apparent that F3H activity may be blocked with moieties that interact directly with F3H to inactivate or impair its hydroxylase activity. In addition, the production of flavonols may be impaired by blocking CHI activity; however this alternative is less preferred since the conversion of chalcononaringenin to naringenin proceeds spontaneously at a low rate in the absence of CHI.

Impairment of male function in plants which lack flavonols as a result of a deficiency in CHS, CHI or F3H activities results in no gross abnormalities in pollen development until immediately prior to dehiscence when the anther morphology deviates from normal in color, shape, and size. At dehiscence the pollen remains clumped within the anther and when viewed microscopically a significant proportion of the grains in a locule appear more shrunken than normal. Although viable pollen is produced and shed, pollen germination and tube growth are greatly impaired both in vivo and in vitro. In addition to functional male sterility, flavonol-deficient plants exhibit some aspects of self-incompatibility, as evidenced by the fact that the pollen can be partially rescued by stigmas of wild type plants, but not by stigmas of flavonol-deficient plants. Although elements of both male sterility and self incompatibility are evident, the features exhibited by pollen from the flavonol-deficient plants clearly constitutes a unique state which is referred to herein as conditional male fertility (CMF).

Plants lacking CHS (and therefore lacking flavonoids) appear normal except for two features: (1) a lack of flavonoid pigmentation and (2) the production of impaired pollen that is entirely dependent on wild pistils (stigma+ style) in order to function.

While CHS deficient plants share a lack of flavonoid pigmentation and pollen function impairment, some differences are evident between plant species. Maize white pollen germinates on the silks and produces a pollen tube whose growth is arrested in the style. Additionally, the maize mutant pollen germinates in vitro and produces a tube nearly as long as wild-type pollen (L. P. Taylor, unpub. obs.). In contrast, pollen from the flavonoid-deficient petunia does not penetrate the stigma nor produce a tube either in vivo or in vitro. This difference between maize and petunia may be explicable in terms of the physiological differences between tricellular (maize) and bicellular (petunia) pollen. Bicellular pollen has a low respiratory rate when shed, forms the second sperm cell after shedding, may be on the sigma several hours before germination and has a low initial pollen tube growth rate. Tricellular pollen, by comparison, undergoes the second mitotic division before anthesis, has a high respiratory rate when shed, germinates within minutes after contact with the stigmatic surface and has a high initial growth rate. Because tricellular pollen is poised to grow rapidly after shedding, maize white pollen tubes grow to a significant length before any mechanism that arrests tube growth is effective.

In flowering plants with alternating generations, the diploid sporophyte produces haploid spores which grow and divide mitotically to produce the gametophyte. Part of the gametophytic life cycle occurs while the developing pollen spore is in intimate contact with surrounding sporophytic tissue. This arrangement has the potential for diploid-haploid interactions. In heterozygous plants this interaction would also include haploid-haploid communication between the two types of gametophytes as represented in FIG. 1. The fact that the petunia flavonoid-deficient male sterility described here is genetically dominant while the maize white pollen male sterility is genetically recessive leads to an interesting conclusion regarding whether the gametophyte or the sporophyte is responsible for the effect. In maize, male sterility is expressed only in plants homozygous recessive for both CHS genes, c2 and Whp. Heterozygotes with either a single functional copy of C2 or Whp produce 100% yellow, fertile pollen grains (Coe et al. 1981). Thus, in the heterozygote either the CHS-positive sporophyte or the 50% CHS-positive gametophytes influence the expression of fertility in the CHS-negative gametophytes. In the transgenic petunia, male sterility is associated with a dominant trait and pollen produced by the heterozygous plants is 100% male sterile. In this case, sterility is caused either by inhibition of the CHS-positive gametophytes by the CHS suppressed gametophytes or by CHS deficiency in the transgenic sporophyte (FIG. 1). The physiological basis for CHS deficiencies causing male sterility appears to be the same in maize and petunia, and in both species it is the sporophyte that causes the sterile phenotype, rather than the gametophyte. Thus, the conditional male fertility associated with CHS deficiency in maize and petunia has a common physiological basis.

The production of conditionally sterile pollen from the flavonol-deficient plants may be used as the basis of an in vitro pollen rescue assay. By incubating the transgenic pollen in germination solution supplemented with purified flavonoids or plant extracts and assaying for enhanced germination frequency and pollen tube growth, specific compounds required for pollen function can be identified. In this manner, it has been determined that the broad family of flavonoid compounds, in general, is not uniformly effective in restoring fertility in CMF plants, but rather that a specific group of fertility restoring flavonol aglycones is effective for this purpose.

Any flavonol which is effective in promoting germination of pollen of a CMF plant may be used in the practice of the invention. It has been found, however, that most members of the relatively large family of flavonoids are ineffective for this purpose. Accordingly, it is a key aspect of the present invention that particular effective fertility restoring flavonols can be identified and used in the restoration of plant fertility in a CMF self sterile condition. In a preferred embodiment of the invention, the fertility restoring flavonol is a compound of the formula:

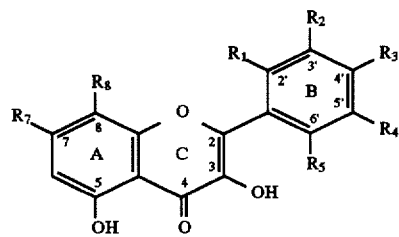

wherein $R_1$, $R_2$, $R_3$, $R_4$, $R_5$, $R_7$, and $R_8$, are hydrogen, hydroxyl or alkoxy having from 1 to 3 carbon atoms. More preferably, not more than two of $R_1$–$R_5$ are hydroxyl or methoxy and the remaining $R_1$–$R_5$ are hydrogen, and $R_7$ and $R_8$ are hydrogen, hydroxyl or methoxy. Presently particularly preferred and representative fertility restoring flavonol compounds of the invention include galangin, kaempferol, iso-rhamnetin, quercetin, and morin which have the general chemical structure set forth above with the following substituents:

TABLE 1

| Flavonol | $R_1$ | $R_2$ | $R_3$ | $R_4$ | $R_5$ | $R_7$ | $R_8$ |
|---|---|---|---|---|---|---|---|
| galangin | H | H | H | H | H | OH | H |
| kaempferol | H | H | OH | H | H | OH | H |
| iso-rhamnetin | H | OCH$_3$ | OH | H | H | OH | H |
| quercetin | H | OH | OH | H | H | OH | H |
| morin | OH | H | OH | H | H | OH | H |

Other flavonols useful in the practice of the invention may be readily determined using the in vitro pollen rescue assay methods set forth herein.

The foregoing may be better understood in connection with the following examples, which are presented for purposes of illustration and not by way of limitation.

EXAMPLE 1

Fertility of Chalcone Synthase-deficient Petunias

Transgenic and inbred V26 petunia were maintained on a 16/8 hour photoperiod in a glasshouse supplemented with metal halide lights at an intensity of 300–600 µmol m$^{-2}$sec$^{-1}$. Inbred V26 is a pigmented line of Petunia hybrids which can produce flavonoids in most plant tissues including pollen, anthers and filaments, and pistil (stigma+style) and is fully self-compatible. The transgenic material analyzed consisted of the two independent transformed regenerants, 218.38 and 218.41 (Napoli C, Lemieux C and Jorgensen R, 1990, "Introduction of a chimeric chalcone synthase gene into petunia results in reversible co-repression of homologous genes in trans," Plant Cell 2:279–289) and individuals from the second backcross generations (BC2) to the parental V26 line (population numbers 2425 through 2435). The T-DNA insertion in these transformants contains CHS cDNA sequences fused to a viral promoter linked to a neomycin phosphotransferase II gene as a selectable marker (Napoli et al. 1990). Crosses were performed by emasculating flowers 24 hours prior to the application of pollen. All transgenic flowers used for crosses showed no visible signs of pigment. Pollen donors were selected from plants that had 2 to 3 dehiscent anthers or dissected from plump, pre-dehiscent anthers as noted.

The transgenic petunia plants 218.38 and 218.41 produce pure white flowers after the introduction of an additional copy of the CHS gene. When CHS expression was examined in the transgenic petals, a 50-fold induction in mRNA compared to the untransformed V26 parent or somatic revertants was detected in both endogenous and introduced CHS genes. The V26 inbred line produces purple anthocyanin pigments in leaves, stems, pedicles, styles and anther filaments, and yellow chalcones in developing anthers. In comparison, the transformed plants have no discernible flavonoid pigments in any of these tissues. The lack of visible pigment was confirmed by HPLC analysis of methanolic extracts, as described in Example 6. Normally, just prior to shedding, petunia anthers filled with mature pollen undergo desiccation. At dehiscence, when the anther case ruptures longitudinally along the stomium, the dehydrated state of the tissue results in the two edges of the anther lobe curling back on one another to expose the pollen grains. Close inspection of the non-pigmented transgenic plants revealed that, in the 48 hours preceding dehiscence, the anthers shrink an average of 40% in length and change in color from creamy-white to tan. In comparison, the anthers of the non-transformed parental line V26 shrank only about 15% and did not undergo a color change, remaining yellow throughout this period. A wide variation in the frequency of dehiscent anthers occurred ranging from 0 to 100% with the higher frequency associated with lowered relative humidity. Although dehiscence may be slightly delayed relative to the V26 parent, the flavonoid-deficient anthers do open to expose normal amounts of pollen which does not appear as light and friable as V26 pollen and remains clumped within the anther case.

No seeds resulted from numerous attempts at self pollination of the flavonoid-deficient progeny of 218.41 using either: (i) pollen from shrunken, tan, dehiscent anthers or (ii) pollen dissected from white, plump, pre-dehiscent anthers (see Table 2, column 5, "Transgenic self crosses: 0 seeds/ pod"). Self crosses of the V26 parent line produced on average 225 seeds per pod. This translates to approximately 17,000 possible seeds in the 75 transgenic petunia self crosses that were attempted. All of the plants listed in Table 2 were tested for female fertility by pollinating stigmas with pollen from inbred line V26. In all cases, pods were produced with the normal complement of seeds, indicating that the CHS deficient plants were female fertile. The reciprocal cross, transgenic flavonoid-deficient pollen onto V26 stigmas resulted in the production of varying quantities of seeds as shown in Table 2.

TABLE 2

Seed Production From Transgenic Pollen Crosses

| | NUMBER OF POLLINATIONS | | | |
|---|---|---|---|---|
| | V26 X transgenic pollen | | | Transgenic |
| Pollen Parent[a] | 0 seeds/pod | 1–150 seeds/pod | >150 seeds/pod | self crosses 0 seeds/pod |
| 02425.1* | 0 | 2 | 0 | 8 |
| 02430.5 | 0 | 5 | 3 | 6 |
| 02430.6 | 2 | 1 | 0 | 6 |
| 02430.8 | ND | ND | ND | 6 |
| 02432.2 | ND | ND | ND | 6 |
| 02435.1 | 0 | 1 | 1 | 6 |
| 02435.2 | 1 | 4 | 1 | 8 |
| 02435.3 | 0 | 1 | 1 | 7 |
| J2425.1* | 0 | 1 | 0 | 1 |

TABLE 2-continued

Seed Production From Transgenic Pollen Crosses

| | NUMBER OF POLLINATIONS | | | |
|---|---|---|---|---|
| | V26 X transgenic pollen | | | Transgenic |
| Pollen Parent[a] | 0 seeds/pod | 1–150 seeds/pod | >150 seeds/pod | self crosses 0 seeds/pod |
| J2428.1 | ND | ND | ND | 6 |
| J2431.2 | 2 | 3 | 0 | 6 |
| J2432.3* | 3 | 0 | 0 | 7 |
| J2430.5* | 3 | 2 | 0 | 2 |

*Flowers on other branches of this plant had some purple pigment in corolla.
[a]At least 4 flowers on each plant listed was pollinated with V26 pollen and all set full seed pods.
Average number seeds/pod = 225.

Of 37 crosses involving 10 different transgenic plants as male parents, 11 produced no pods, 20 produced pods with less than 150 seeds per pod and 6 produced pods with greater than 150 seeds per pod. This averages to approximately 60 seeds per pod or a 70% reduction in seed set. These results indicate that while pollen from the flavonoid-deficient plants is non-functional on flavonoid-deficient stigmas it is partially functional on wild type stigmas, the state we termed herein as conditional male fertility (CMF). The wide variation in the number of seeds set per pollination in these outcrosses is possibly due to environmental and/or developmental factors.

It is unlikely that CMF is due to the insertion of T-DNA into a gene required for male fertility since two independent transformants, 218.38 and 218.41, both display the same features: a complete lack of flavonoid pigmentation and identical dominant male sterile phenotypes. Additional evidence for this conclusion comes from the observations of Napoli et al. (1990) that the transformed regenerants sometimes revert somatically to fully pigmented plants but retained the transgene, indicating that the presence of the transgene alone does not suppress endogenous CHS expression. Further observation and crosses of these somatic revertants indicate that they are fully male fertile. Given the similarity with white pollen in maize, CMF in petunia appears to be caused by a deficiency in flavonoids, such as that caused by a suppression of CHS or F3H gene expression.

EXAMPLE 2

Pollen Germination and Tube Growth

In vitro germination was performed on freshly collected pollen in simplified Brewbakers medium as described in Mulcahy G B and Mulcahy D L, 1988, "The effect of supplemented media on the growth in vitro of bi- and trinucleate pollen," *Plant Science* 55:213–216 (hereinafter sometimes referred to as "germinating medium" or "GM"). Pollen from a single anther was placed in a microtiter well with 50 μl of media, rocked at room temperature for 6 to 8 hours and photographed with Kodak technical pan film.

In vivo pollen tube growth was measured 48 hours post-pollination as described in Herrero M. and Dickinson H. G., 1979, "Pollen-pistil incompatibility in Petunia hybrids: changes in the pistil following compatible and incompatible intraspecific crosses," *J Cell Sci* 36:1–18. Callose plugs were visualized by epifluorescence generated by excitation at 355–425 nm (D cube) and suppressing wavelength 460 nm from a Leitz Aristoplan. Specimens were photographed with Ektachrome T 160 film and prints made from an internegative.

Pollen viability was determined with the fluorochromatic procedure (FCR) (Heslop-Harrison J. and Heslop-Harrison Y., 1970, "Evaluation of pollen viability by enzymatically induced fluorescence; intracellular hydrolysis of fluorescein diacetate," *Stain Technol.* 45:115–120) by incubating freshly dehiscent pollen in a solution of carboxyfluoresceine acetate (1 mM) in germination media. Epifluorescence was visualized as described above.

Callose Production

Petunia pollen tubes normally penetrate the stigma about one hour after germination (Herrero and Dickinson, 1980) and grow downward through the styler tissue to deposit the two sperm cells in the embryo sac. Callose is a polysaccharide polymer linked in β(1K3) glycosidic linkages and plugs of this material are normally deposited at regular intervals down the growing pollen tube. Callose is visualized by its distinctive fluorescence after staining with decolorized aniline blue (Currier 1957; Eschrich and Currier 1964). The germination and growth of pollen tubes in self crosses of the CHS-deficient flowers of Example 1 and in backcrosses of the same plants with V26 pollen were examined. Pistils were harvested 48 hours after pollination, stained with decolorized aniline blue and examined by fluorescent microscopy. A regular pattern of callose deposits was observed all the way down the style in the squashes of flavonoid-deficient pistils pollinated by V26. On the other hand, no callose was seen in the pistils of the self pollinated petunias even though copious amounts of pollen was present on the stigma.

Pollen Morphology and Germination

A microscopic examination of freshly shed pollen from the flavonoid-deficient plants of Example 1 was made and did not reveal any gross abnormalities. Petunia pollen readily germinates and produces a tube when incubated in a simple liquid medium. Germinated pollen from each of the BC2 families (2425 to 2435) to V26 pollen were compared in vitro. A typical representative is shown in FIG. 2. As shown in FIG. 2, after 6 hours of growth many mutant pollen grains had attempted germination as noted by the pronounced swelling around one of the germination pores (arrows, FIG. 2), but at most only 2% of the pollen grains from the flavonoid-deficient plants produced a tube of any length. Of the pollen grains that did produce measurable tubes, the length was less than 20 % the length of V26 pollen tubes grown under identical conditions.

To determine whether the pollen produced and shed by the flavonoid-deficient plants was viable and therefore capable of germination and pollen tube growth, a fluorochromatic analysis (FCR) for viability on freshly shed transgenic and V26 pollen was performed. This test depends on the uptake of a fluorescein diacetate compound into the pollen grain with subsequent conversion to fluorescein by intracellular enzymes. Fluorescein is highly polar and remains sequestered, most likely in the vegetative cell cytoplasm, where it is visualized by fluorescent microscopy. Inbred V26 pollen consists of a high proportion (up to 40%) of abnormally small, FCR negative grains which entirely lack any internal features. Several grains of this type can be seen in FIG. 2A, including two in the center of the photograph. This population never germinates and is most likely aborted grains. Of the remaining grains (60%), almost all showed a positive FCR test, indicating the presence of intact plasma membranes and active cytoplasmic esterases. Pollen from the mutant anthers retained the high proportion of shrunken, aborted grains. Of the remaining normal appearing grains, more than 90% were FCR positive. The fact that most of the pollen produced by the flavonoid-deficient plants was viable and metabolically active indicates that some aspect of CHS activity is required for normal pollen germination and tube growth.

EXAMPLE 3

Microscopic Observations of Anther Development

To determine if the lack of CHS activity during microsporogenesis altered the cellular architecture of the developing pollen grains or anther tissues, pollen development in V26 and CHS deficient plant O2425.1 was compared. Anthers from a developmentally staged series of petunia buds ranging in length from 0.1 to 6 cm were harvested, fixed in 2% paraformaldehyde, 1.25% gluteraldehyde in Pipes, pH 7.2, embedded in Spurrs resin, and 1 μm sections were stained with toluidine blue. Photomicrographs were made with Kodak technical pan film. Histologically this represents all stages of microsporogenesis, from the earliest evidence of archesporial tissue differentiation to pre-dehiscent anthers filled with mature pollen. Close attention was given to the development and subsequent disintegration of the tapetum, since this tissue is thought to be the source of pollen flavonoids. At all stages the transgenic anther and developing microspores showed no gross histological differences when compared to V26. Additional sections were taken from the flavonoid-deficient anthers during the transition from plump, white to shrunken, tan and compared to similar stages in V26 (FIG. 3). Preceding dehiscence the cells of the endothelial layer normally expand radially, thicken, and deposit material which is thought to be involved in the mechanism of anther rupture (Cutter, E. G., 1978, "Plant Anatomy: Experimentation and Interpretation. Part 1," *Cells and Tissues.* 2nd ed., London: Arnold). This layer is not continuous, being absent in the area surrounding the stomium. The sections of the shrunken, tan anthers showed no gross abnormalities to the endothelial layer, stomium, or cuticle surrounding the anther. However, when compared to V26 pollen (FIG. 3, Column "V26") a higher proportion of shrunken grains devoid of internal features were present in the locules of the transgenic plants and the larger grains appeared more heterogeneous in size, shape, and staining reaction (FIGS. 3C and 3D). The heterogeneity shown in FIGS. 3C and 3D may be accounted for by the fact that pollen is normally shed in a highly dehydrated state and undergoes rapid rehydration on the stigma. flavonoid-deficient pollen may be shed in a much more dehydrated state than normal, and when placed in liquid germination medium, appears to rehydrate to a normal appearance.

EXAMPLE 4

Petunia Flavonoid Extracts

Analyses of petunia pollen extracts have identified the major flavonoids as 3-0-glycosides of quercetin and kaempferol, 4,2',4',6'-tetrahydroxychalcone, and a dihydroflavonol, taxifolin (Zerback, R., Bokel, M., Geiger, H. and Hess, D., 1989, *Phytochemistry* 28:897–899; Zerback, R., Dressier, K. and Hess, D., 1989, *Plant Science* 62:83–91; De Vlaming, P. and Koh, K. F. F., 1976, *Phytochemistry* 15:348–349). Maize pollen contains at least 10 glycosides of kaempferol, quercetin, and isorhamnetin (Ceska, O. and Styles, E. D., *Phytochemistry* 23:1822–1823) Aqueous extractions from both wild type and inbred petunia line V26 were made by mascerating stigmas with forceps or vortexing a pollen suspension in PEG 4000 media (W.

Jahnen, W. M. Lush, A. E. Clarke, 1989, *Plant Cell* 1:501), hereafter referred to as GM, centrifuging 5 min in a microfuge, and applying aliquots of the supernatant directly to a CMF pollen suspension in GM in a 96 well microliter plate. Methanol extractions were made following the same protocol except the extract was dried under vacuum and resuspended in GM before addition to the pollen suspension. The initial rescue experiment elicited a 33% germination rate using 20 µl (one-fifth total volume) of an aqueous extract prepared from ten V26 stigmas. As a control, extracts were prepared in a similar manner from stigmas and pollen of the CMF plants. In pollen germination assays only extracts from V26 stigmas and pollen were able to restore germination and tube growth to the flavonoid-deficient pollen. The wild type and CMF pollen and stigma extracts were analyzed as follows. Stigmas or pollen were extracted first with 50% methanol, followed by 100% methanol, and the extracts were pooled and concentrated. Aglycones were produced by acid hydrolysis: the extract was mixed v/v with 4N HCl, sealed in a 2 ml ampule and hydrolyzed in boiling water for 40 min. Replicate samples were injected into a reverse-phase C18 column (Phenomenex Spherisorb 5 ODS 2 250×4.6 mm). Solvent A was 5% acetic acid and solvent B consisted of 5% acetic acid in 80% acetonitrile. Each run consisted of a 6 min isocratic gradient (20% B), followed by a 20 min linear gradient to 95% B and terminated isocratically at 95% B for 14 min. The solvent flow rate was 0.5 ml/min at room temperature. Detection was at 360 nm with a Hewlett Packard model 1040A photodiode array detector. Kaempferol was detected in the wild type stigma extracts at 60 ng stigma, and quercetin at substantially lower levels. Identical extracts from a pool of 150 CMF stigmas or from 500 CMF anthers yielded no peaks giving a typical flavonoid spectra.

Treatment of the wild type stigmatic extract with protein digesting enzymes, heat, and passage through molecular sizing membranes indicated that the active compound was a small non-proteinaceous molecule. The molecular weight of the active compound was estimated by passing the extract through a 3000 dalton molecular weight cutoff filter (Centricon-30 filter, Amicon) and establishing that the pollen rescue activity passed through the filter. Aqueous extracts of V26 stigmas and pollen were treated with 0.025 units of papain for 30 min at 37° C. in a 100 µl reaction volume. Enzyme activity was verified by treating BSA (0.5 mg/ml) under the same conditions and by examining the digestion products by SDS-polyacrylamide gel electrophoresis (PAGE). Neither the protease nor a heat treatment (100° C., 5 min) eliminated the ability of the extracts to rescue CMF pollen germination and tube growth.

Collectively, these results indicate that the flavonoids present in wild type pollen play a role in pollen germination and that the wild type stigma contains similar compounds which can compensate for the lack of flavonoids in the CMF pollen.

EXAMPLE 5

Flavonol Rescue of CMF Fertility

Figures 4A, 4B, 4C:
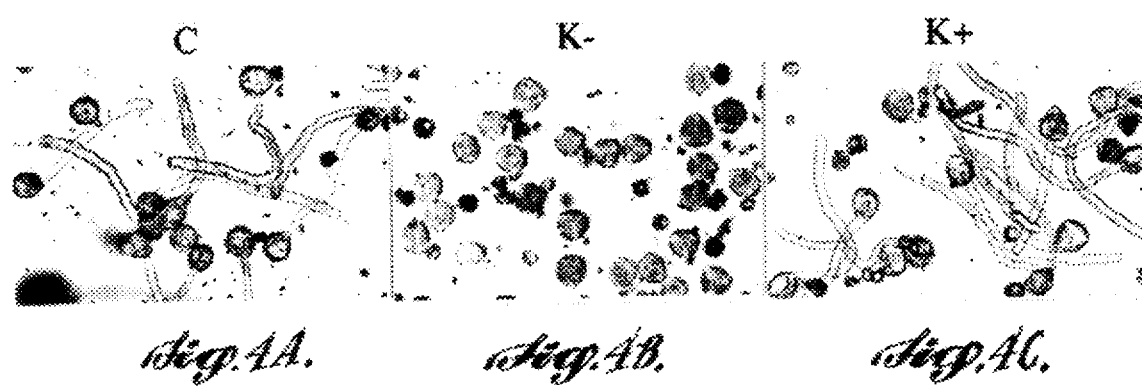
FIG. 4 is a photographic representation of the restoration of pollen germination and tube growth to petunia CHS-deficient pollen by the fertility restoring flavonol, kaempferol. Pollen was collected from conditionally male fertile anthers, suspended in germinating medium, and kaempferol (K+, FIG. 4C) or DMSO (K−, FIG. 4B) added to 1 μM final concentration. Representative fields of pollen are pictured after 4 hours of incubation. The germination and tube growth observed in the kaempferol rescued CMF pollen (FIG. 4C) is indistinguishable from the wild type V26 control (C, FIG. 4A) which received DMSO only. The non-supplemented CMF pollen (FIG. 4B) shows swelling at the germination pore in some grains but no pollen tubes are extruded.

Biochemical complementation of the flavonoid-deficient pollen of Example 1 was achieved by adding a low concentration (1 µM) of kaempferol, a flavonol aglycone, to a suspension of CMF pollen in germination medium (GM). As shown in FIG. 4, side-by-side comparisons made throughout a 12 hour growth period confirmed that germination initiated simultaneously and that tube growth proceeded at the same rate and to the same extent in the rescued CMF pollen (K+) compared to wild type V26 pollen which received no flavonol supplement (C). The rescue was nearly complete; the flavonoid-supplemented pollen showed an 80% germination frequency relative to V26 pollen. CMF pollen to which only the DMSO solvent was added (K−) showed no significant germination (1–2%) and the pollen tubes, if they germinated at all, never progressed more than 2 pollen grain diameters.

Figure 5A:
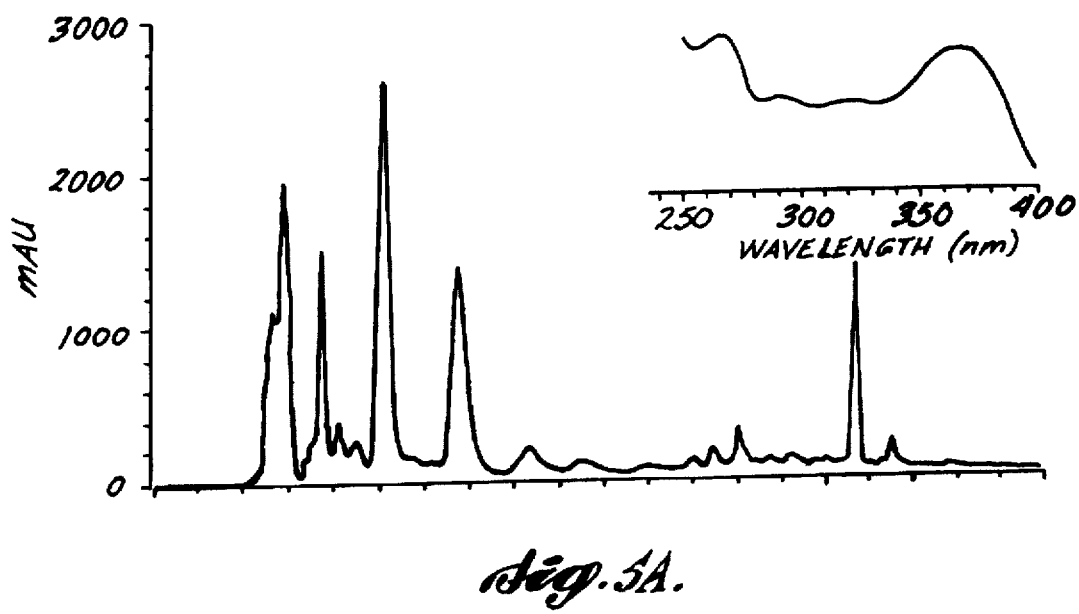
FIGS. 5A and 5B show an HPLC profile of methanolic extracts of wild type V26 stigmas (FIG. 5A) and CMF stigmas (FIG. 5B). Absorption at 360 nm of 100 μl aliquots of extracts prepared from 150 stigmas and fractionated in a methanol-water gradient on a reverse-phase $C_{18}$ column. The inset of FIG. 5A is the UV/visible spectrum of the peak at 33.17 min and is identical to that produced by an authentic kaempferol standard. An HPLC profile and UV/visible spectrum of an acid hydrolyzed V26 stigma extract indicates that the major peaks at retention time 7.43, 10.10, 13.46 and 16.65 are glycosides of kaempferol and quercetin.
Figure 5B:
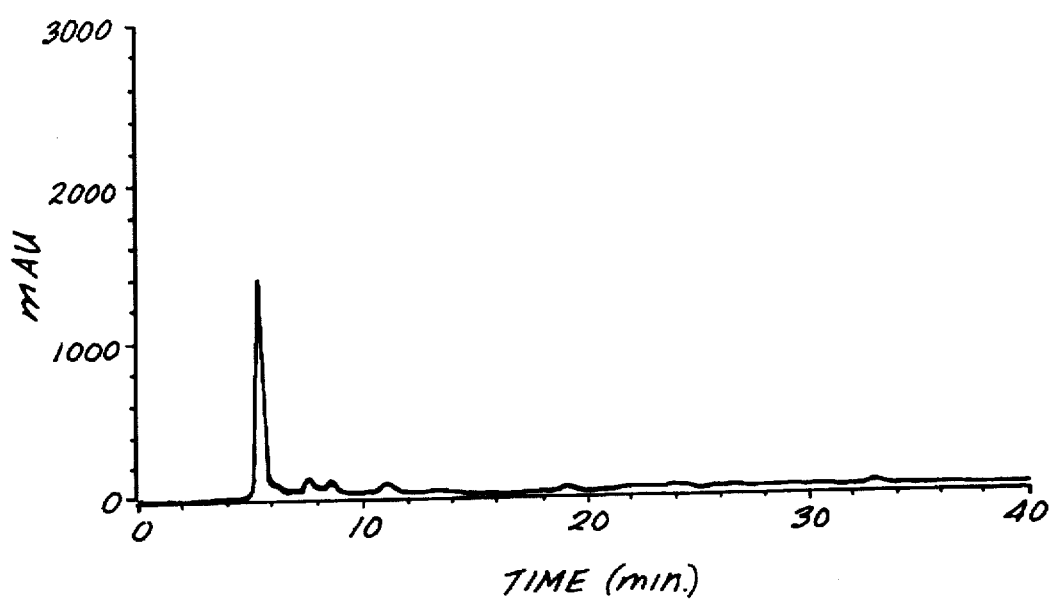
Figure 6:
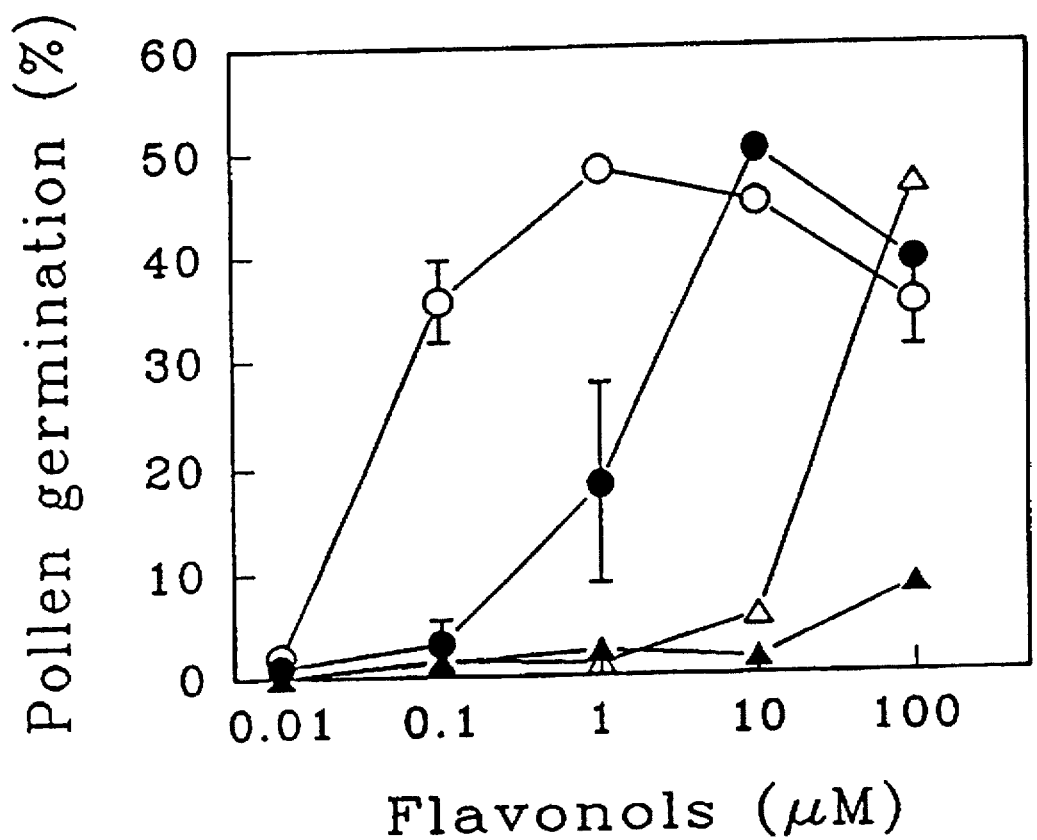
FIG. 6 is a graphical representation of pollen germination frequency as a function of increasing flavonol aglycone concentration, in which kaempferol (open circles), morin (closed circles), myricetin (open triangles) and 3-hydroxyflavone (closed triangles) were added to germinating medium (GM) at the indicated final concentrations and germination was scored after 4 hours of incubation. The mean germination frequency measured in three separate experiments is plotted with the standard error of the mean (SEM). SEM values <1.4 are not visible. The germination frequency of the wild type control V26 pollen is typically 75% and the non-rescued DMSO-treated CMF pollen yields between 1–2 % pollination.

To confirm that wild type stigma extracts which are capable of rescuing pollen germination and tube growth contain kaempferol, unhydrolyzed extract was fractionated by HPLC and analyzed by UV/visible absorption spectroscopy. A peak with a retention time and typical flavonol spectra (absorption maxima around 260 and 360 nm) was detected in the V26 stigma extract (FIG. 5A and inset). This putative kaempferol peak was collected, evaporated to dryness, resuspended in DMSO and added to the in vitro GM media where it elicited a full germination and tube growth response from the CMF pollen. Re-chromatography of this active fraction with an authentic kaempferol standard confirmed its purity and identity. From this analysis of 150 stigmas, the amount of kaempferol in a V26 stigma is calculated to be 60 ng/stigma. By assuming a stigma volume of 34 µl (volume displacement), the flavonol concentration in a V26 stigma is about 6 µM, a level which is capable of eliciting a strong germination response. An identical analysis on extracts from a pool of 150 CMF stigmas or from 500 CMF anthers yielded no peaks giving a typical flavonoid spectra (see FIG. 5B). Extracts from V26 pollen and anthers produced a chromatogram similar to that shown in FIG. 5A and the eluent peak, with a retention time and UV/visible spectrum indicative of kaempferol, when added to CMF in GM fully stimulated pollen germination. This analysis confirms that kaempferol is present in wild type pollen and anthers.

Structural features required for pollen rescue activity. Wild type pollen and stigma extracts from petunia contain other compounds in addition to kaempferol which may also stimulate pollen germination and tube growth (see FIG. 5A). Therefore representative compounds from all the major classes of flavonoids: flavones, flavanones, flavonols, isoflavonoids, chalcones, anthocyanins, and catechins were assayed for pollen rescue activity, as follows. Petunia pollen grains were suspended in PEG 4000 germination medium (GM) at a density of 1–2×10$^4$/ml, and 100 µl aliquots of the suspension were placed in wells of a 96 well microliter plate and were incubated at room temperature with shaking at 150 rpm. Any supplements were added directly to the GM before addition of the pollen. Stock solutions of flavonoids and other chemicals were made directly in dimethylsulfoxide (DMSO) and added to each well to the final concentrations indicated in the following Table 3. The concentration of DMSO was held constant in each assay at 1%. Pollen was scored as germinated when the tube was more than 1 pollen grain diameter long. Practically all grains that germinate go on to produce a tube longer than 5 pollen grain diameters. Petunia V26, as described in Example 1, produces two types of mature pollen; about 25% of the grains are small with no internal features and they never germinate in vitro. Therefore, complete germination in V26 occurs when 75% of the total pollen grains have germinated. The CMF petunia pollen of Example 1 maintains this same ratio. In most rescue experiments the maximum germination frequency was 89% of the viable grains. After 4 hours incubation a minimum of 1000 pollen grains were scored in each assay. The lowest concentration of the tested compounds required to obtain a germination response are set forth in the following Table 3, wherein NR indicates no response. Compounds which caused <20% germination at 100 µM are indicated as >100 µM. In addition to the compounds listed in Table 3, the non-flavonoids p-coumaric acid, salicylic acid, hydroquinone, chlorogenic acid, dihydroascorbic acid, naphthylphthalmic acid (NPA), 1-napthhthaleneacetic acid (NAA), indol-3-acetic acid (IAA) and gibberellic acid (GA3) were tested and produce no response.

TABLE 3

| Compound | Substituent Carbon | | | | | | | Concentration for response (µM) |
|---|---|---|---|---|---|---|---|---|
| | 3 | 5 | 7 | 2' | 3' | 4' | 5' | |
| Flavonols ($C_2$=$C_3$) | | | | | | | | |
| Galangin | OH | OH | OH | | | | | 1 |
| Kaempferol | OH | OH | OH | | | OH | | 1 |
| Isorhamnetin | OH | OH | OH | | OCH$_3$ | OH | | 1 |
| Quercetin | OH | OH | OH | | OH | OH | | 10 |
| Morin | OH | OH | OH | OH | | OH | | 10 |
| Myricetin | OH | OH | OH | | OH | OH | OH | 100 |
| Fisetin | OH | | OH | | OH | OH | | 100 |
| 3-hydroxyflavone | OH | | | | | | | >100 |
| Dihydroflavonol ($C_2$-$C_3$) | | | | | | | | |
| Taxifolin | OH | OH | OH | | OH | OH | | >100 |
| Flavones ($C_2$=$C_3$) | | | | | | | | |
| Flavone | | | | | | | | NR |
| 7-Hydroxyflavone | | | OH | | | | | NR |
| Apigenin | | OH | OH | | | OH | | NR |
| Luteolin | | OH | OH | | OH | OH | | NR |
| Flavanones ($C_2$-$C_3$) | | | | | | | | |
| Flavanone | | | | | | | | NR |
| Naringenin | | OH | OH | | | OH | | NR |
| Eriodictyol | | OH | OH | | OH | OH | | NR |

As set forth in Table 3, the R-substituent positions correspond to flavanoids of the formula:

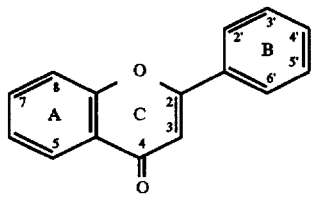

As can be seen from Table 3, the aglycone flavonols successfully restored maximal germination frequency and tube growth capacity to the CMF pollen but among the other classes of flavonoids only the closely related dihydroflavonol, taxifolin, produced a modest (~18%) response at 100 µM. Additionally, several classes of non-flavonoid compounds were tested including phenolic acids, anti-oxidants, and plant growth regulators but none were able to rescue pollen germination. Hence, the ability to rescue pollen function at physiologically relevant concentrations resides in the flavonols.

From the range of flavonoids tested, five general structural characteristics appear to be necessary for maximal pollen germination and tube growth. There are absolute requirements for an unsubstituted hydroxyl group at the 3-carbon position and for a keto group at position 4 in the C ring. A maximal response depends on an unsaturated bond between carbons 2 and 3 in the C ring and the degree of hydroxyl group substitutions in the A and B rings. Most interestingly, flavonols glycosylated through the 3 hydroxyl position are inactive although they are by far the most abundant form of flavonols found in plant tissues, including petunia pollen and stigma. No pollen germination was obtained when quercetin-3-O-glucoside and rutin (quercetin-3-O-rhamnoglucoside) were tested at concentrations up to 100 µM.

The requirement for a keto group at position 4 in ring C is indicated by the fact that catechin, which has no keto group, lacks activity. A comparison of the relative efficiencies of taxifolin (~18% at 100 µM) and quercetin (~50% at 10 µM) shows that a double bond between carbons 2 and 3 in the C ring increases the response by about 30-fold. A comparison of quercetin with fisetin or with 3-hydroxyflavone, shows that each additional hydroxyl group at either position 5 or 7 on the A ring increases the response approximately 10-fold. This increase may depend largely on the stabilizing effect of a interaction between the 5 hydroxyl group and the adjacent keto group in ring C. Finally, hydroxyl substitutions on the B ring are not necessary for full activity, and in fact increasing the number of groups actually causes a decrease in the activity (compare kaempferol with quercetin and muricetin). This difference could be due to poor uptake or an increase in non-specific binding caused by the more polar nature of the flavonols with numerous hydroxyl groups.

Some non-active flavonoids have been reported to antagonize active flavonoid-induction of nodulation genes in the Rhizobium-legume system (Djordjevic, M. A., Redmond, J. W., Batley, M. and Rolfe, B. G., 1987, EMBO 6:1173–1179; Peters, N. K. and Long, S. K., 1988, Plant Physiology 88:396–400). The compounds that were non active in rescuing pollen function were tested for their ability to antagonize the action of the flavonol aglycones, as follows. CMF pollen, as described in Example 1, in GM was exposed to inactive compounds at concentrations of 1 and 10 µM for 30 minutes before adding kaempferol to 1 µM. The experiment was also performed by simultaneously adding both the inactive compound and kaempferol, at 1:1 or 10:1 ratios, to the pollen suspension. The pollen germination frequency was scored after 4 hours incubation and no antagonizing action was detected in any of the combinations tested. The following inactive compounds were analyzed: apigenin, chalcone, eriodictyol, flavone, flavanone, luteolin, naringenin, catechin, chlorogenic acid, p-coumaric acid, hydroquinone, and salicylic acid.

EXAMPLE 6

UV Effects

In part because of their UV light absorbing capabilities, flavonoids are postulated to function as UV protectants in plants (W. Jahnen and K. Hahlbroch, 1988, Planta 173:453 and references therein). To determine if the lack of germination in the flavonoid-deficient pollen was due to UV effects, dark germination experiments were performed with three variations. Pollen was harvested either from (1) flowers that were collected and stored (in water) in complete darkness for 24 hrs or (2) freshly picked flowers. From these two sources pollen suspensions in GM with or without flavonols were prepared in a darkroom using a red safe light.

The third variation involved preparing the pollen suspension from the freshly harvested flowers in the light but adding the flavonols solution in the dark. All specimens were wrapped in foil and then incubated as described in Example 5. There was no detectable effect of light on germination frequency for either the V26 control or the flavonoid deficient pollen, with or without added flavonols.

To determine if UV light affected self fertilizations, mature petunia plants were grown for several weeks under a 610 nm filter as described in L P. Taylor and W. R. Briggs, 1990, *Plant Cell* 2:115. Petunia buds take about 2 weeks to form and mature, therefore only those buds that formed after the plants were placed under the filter, and thus were exposed to no light below 610 nm, were tested and self fertilized. No seed set occurred in any of the CMF self crosses (10 trials) but all V26 control self crosses performed under the same conditions set full seed pods.

EXAMPLE 7

Effect of Flavonol Exposure Time

The amount of flavonoid exposure required for complete germination and maximal tube growth was determined by varying the time the germinating pollen was in the presence of flavonol. A concentration of kaempferol calculated to give near maximal rescue, yet easily removed by washing (0.5 µM final), was added to a 60×15 mm petri dish containing a suspension of 5 ml of flavonoid-deficient pollen in GM, and the resulting suspension was continuously rotated at 150 rpm. At times indicated in Table 4, 400 µl aliquots were taken, centrifuged, washed in 1 ml of GM to remove the kaempferol, recentrifuged, resuspended in 400 µl GM, and split into two portions. One 100 µl aliquot was again supplemented to 0.5 µM kaempferol (control) but the other portion was allowed to continue growth without additional flavonol exposure (treated). Growth was allowed to proceed for a total elapsed time of 4 hours from the formulation of the original suspension, then germination frequency and tube length were scored in both treated and control germinations. The results are shown in the following Table 4:

TABLE 4

| Treated Pollen | | Control | |
|---|---|---|---|
| Exposure time (min) | Germination (%)* | Tube Length** | Germination (%)* |
| 0 | 3.7 +/− 1.5 | 2x | 48.3 +/− 2.5 |
| 10 | 6.6 +/− 2.7 | 2x | 55.5 +/− 8.6 |
| 20 | 15.7 +/− 9.2 | 2–3x | 47.9 +/− 7.0 |
| 30 | 13.8 +/− 1.7 | 2–3x | 44.4 +/− 3.7 |
| 60 | 38.9 +/− 2.9 | 3x | 48.4 +/− 1.3 |
| 120 | 47.3 +/− 3.6 | >5x | 47.7 +/− 2.2 |

*mean +/− SEM, n = 3
**relative to pollen grain diameter

As seen in Table 4, a measurable increase in germination was detected with an exposure time as short as 10 min (Table 1). An exposure time between 1 to 2 hours was required for maximal germination frequency and tube length.

EXAMPLE 8

In Vivo Fertility Rescue

The ability to restore self fertility to the CMF petunia by supplying a flavonol aglycone to the pollen at the time of pollination was tested by scoring for successful fertilizations resulting from self crosses of the CMF petunia done in the presence of added flavonols. Prior to self pollinating, flavonol aglycones were applied either (i) directly to the stigma or (ii) mixed with the freshly collected pollen. The most successful technique, measured by the quantity of seed set, required application of the flavonol to the stigma 12–16 hours prior to self pollination. 47 self crosses were performed with added kaempferol or quercetin, and nearly 60% (27 out of 47) produced seed pods. The number of seeds per pod varied from 31 to 287, and in germination tests >90% of the seeds in any single pod were viable. All self crosses done without added flavonols (>30 trials) yielded no seed set.

The dominant CMF trait exhibited by the flavonoid-deficient petunia is tightly linked to a second dominant gene conferring kanamycin resistance (KAN) (Napoli C, Lemieux C and Jorgensen R, 1990, "Introduction of a chimeric chalcone synthase gene into petunia results in reversible co-repression of homologous genes in trans," *Plant Cell* 2:279–289). The KAN marker was used to test for segregation of the CMF character in the seeds produced by self crossing the flavonoid-deficient plants in the presence of added flavonol. Freshly harvested seeds were surface sterilized in 20% bleach, washed with sterile water and soaked for 30 min in 100 ppm GA3 solution before plating on germination plates (1×MS, 3 mM MES [pH 5.6], 1×B5 vitamin mix, 3% sucrose and 0.2% solidifying agent) containing 100 µg/ml kanamycin. After growth at 23° C. supplemented with a 16/8 hour photoperiod, resistance to kanamycin was scored by screening for the presence of true leaves and lateral roots, neither of which were produced by seedlings sensitive to kanamycin. In the following Table 5, P-value represents the observed level of significance for a one degree of freedom chi-square goodness-of-fit test.

TABLE 5

| | Seedlings | | | |
|---|---|---|---|---|
| Pod | Total | KAN | KAN | P (3:1) |
| 1 | 75 | 58 | 17 | 0.74 |
| 2 | 65 | 50 | 15 | 0.83 |
| 3 | 81 | 59 | 22 | 0.75 |

As shown in Table 5, seeds germinated in the presence of 100 µg/ml kanamycin segregated in a 3:1 ratio of KAN resistance:sensitive as expected for a heterozygous dominant trait, as shown in Table 5.

EXAMPLE 9

Field Trial

A field trial was performed using a naturally occurring flavonoid-deficient maize mutant, white pollen, defective in CHS activity, which produces white, non-functional pollen, and is self sterile (E. H. Coe, S. M. McCormick, S. A. Modena, 1981, *J. Hered.* 72:318). The maize white pollen plants used had stable recessive mutations at C2 and Whp introgressed into a W23 inbred background. The white pollen plants (c2/c2 whp/whp) were maintained by crossing with pollen from isogenic plants carrying a single functional copy of CHS (C2/c2 whp/whp). The plants were male sterile in self and sibling crosses and produced no visible flavonoid pigments in any tissues, including pollen and seeds. Standard genetic field practices were employed to insure that no contaminating pollen reached the silks of the white pollen plants. In addition, the white pollen block was surrounded with a pigmented kernel variety so that any contaminating kernels would immediately be recognized. Mutant white pollen from 50-100 plants was collected from the tassel bags, pooled, and divided into 2 portions. One portion was used "as is" for crosses and the other was mixed in an approximate 20:1 ratio with dry flavonols (either quercetin, kaempferol, or a 50:50 mixture of the two). Prepared white pollen silks were pollinated with either the untreated or the flavonol-supplemented white pollen and bagged immediately. The mature ears were harvested 45 days after pollination. White pollen crosses usually set ~200 kernels per ear and this number was routinely obtained in the biochemically complemented self-crosses. A total of 45 self crosses were performed in the presence of added flavonols and all of them (100%) produced fully filled ears while self crosses (45 trials) done without added flavonoids showed seed set less than 1% of normal.

The foregoing experiments confirm that flavonols are required for pollen function as follows: (i) methanol and aqueous extracts of wild type stigmas and pollen can fully restore germination and tube growth to flavonoid-deficient pollen; (ii) these extracts contain the same flavonols that show activity in the in vitro fertility rescue assay described herein; (iii) the ability to rescue pollen germination and restore full tube growth in vitro and full seed set in vivo is restricted to a specific class of flavonoid, the flavonol aglycones; (iv) the effective concentration of flavonol varies with structural features, but several compounds show a pronounced effect at levels less than 10 µM, well within physiological concentrations of these compounds.

Flavonoids are produced by virtually all classes of plants from liverworts, mosses, and ferns to gymnosperms and angiosperms. Past flavonoid surveys often used dried leaf or root tissue from herbarium specimens; consequently, we do not have a good indication of how widespread is the occurrence of pollen flavonoids. Their ubiquitous presence in plant tissues and the fact that flavonoids have been identified in pollen extracts from several widely divergent species, indicate that flavonoids are a universal constituent of pollen. Most plant flavonols occur as the 3-0-glycosylated species (J. B. Harborne and C. A. Williams, 1988, in *The Flavonoids, Advances in Research Since* 1980 J. B. Harborne, Eds. (Chapman and Hall, London) chaps. 7, 8), and this is the predominant form in petunia pollen (O. Ceska and E. D. Styles, 1984, *Phytochemistry* 23:1822 ). Only the aglycone form can rescue pollen function which suggests that either low non-detected levels of the aglycone are normally present, or a glycosidase activity is required to produce the aglycones that are necessary for fertilization.

Pollen provides the natural access point to manipulate the fertilization process. The loss of flavonol activity resulting in CMF plants acts as a natural gametostat and not a gametocide. Full male function can be restored by external application of flavonols to the flavonoid-deficient pollen. In addition to the identification of a factor involved in higher plant fertilization, a significant benefit of the present invention is the development of a reversible male sterile system for the production of hybrid seed.

While the preferred embodiment of the invention has been illustrated and described, it will be appreciated that various changes can be made therein without departing from the spirit and scope of the invention.

What is claimed is:

1. A method of regulating the fertility of a plant comprising blocking production or activity of flavonols at the site of pollen development in the plant to obtain a conditionally male fertile plant having inhibited germination and tube growth ability, and then contacting the pollen or stigma of the conditionally male fertile plant with a compound selected from the group consisting of galangin, kaempferol, iso-rhamnetin, quercetin, morin and mixtures thereof to restore germination and tube growth ability in the plant.

2. The method of claim 1 wherein the production of flavonols in the plant is blocked by inhibiting the production or activity of an enzyme in the flavonol biosynthetic pathway in the plant.

3. The method of claim 2 wherein the production of flavonols in the plant is blocked by inhibiting the production or activity of flavanone-3-hydroxylase in the plant.

4. The method of claim 2 wherein the production of flavonols in the plant is blocked by inhibiting the production or activity of chalcone synthase in the plant.

5. A method of restoring plant fertility to a flavonoid-deficient, conditionally male fertile plant comprising contacting the pollen or the stigma of the plant with an amount of a fertility restoring flavonol effective to enhance germination or tube growth of the pollen of the plant, wherein the fertility restoring flavonol is selected from the group consisting of galangin, kaempferol, iso-rhamnetin, quercetin and morin.

* * * * *